(12) United States Patent
Tracey (10) Patent No.: US 8,708,376 B2
(45) Date of Patent: Apr. 29, 2014

(54) MEDIUM CONNECTOR (75) Inventor: Brian D. Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 127 days.

(21) Appl. No.: 12/249,340

(22) Filed: Oct. 10, 2008

(65) Prior Publication Data
US 2010/0089475 A1 Apr. 15, 2010

(51) Int. Cl.
F16L 25/00 (2006.01)

(52) U.S. Cl.
USPC .............................. 285/332; 285/921; 604/192

(58) Field of Classification Search
USPC .......................... 285/139.3, 921, 332; 604/192
See application file for complete search history.

(56) References Cited

U.S. PATENT DOCUMENTS

| | | | |
|---|---|---|---|
| 3,631,847 A | 1/1972 | Hobbs, II | |
| 3,692,027 A | 9/1972 | Ellinwood, Jr. | |
| 3,752,510 A * | 8/1973 | Windischman et al. | ... 285/334.4 |
| 3,811,121 A | 5/1974 | Heim et al. | |
| 3,811,122 A | 5/1974 | Raber et al. | |
| 3,837,339 A | 9/1974 | Aisenberg et al. | |
| 3,887,393 A | 6/1975 | La Rue, Jr. | |
| 3,951,147 A | 4/1976 | Tucker et al. | |
| D248,873 S | 8/1978 | Raitto | |
| 4,123,631 A | 10/1978 | Lewis | |
| 4,146,029 A | 3/1979 | Ellinwood, Jr. | |
| 4,150,672 A | 4/1979 | Whitney et al. | |
| D254,446 S | 3/1980 | Raitto | |
| 4,206,274 A | 6/1980 | Peels | |
| 4,215,701 A | 8/1980 | Raitto | |
| 4,267,836 A | 5/1981 | Whitney et al. | |
| 4,269,908 A | 5/1981 | Stemme | |
| 4,270,532 A | 6/1981 | Franetzki et al. | |
| 4,273,121 A | 6/1981 | Jassawalla | |
| 4,282,872 A | 8/1981 | Franetzki et al. | |
| 4,296,949 A * | 10/1981 | Muetterties et al. | ............ 285/18 |
| 4,331,262 A | 5/1982 | Snyder et al. | |
| 4,371,594 A | 2/1983 | Ohara et al. | |

(Continued)

FOREIGN PATENT DOCUMENTS

| | | |
|---|---|---|
| DE | 4329229 A1 | 3/1995 |
| DE | 19627619 A1 | 1/1998 |

(Continued)

OTHER PUBLICATIONS

A Preliminary Report on Patentability from corresponding International Appln. No. PCT/US2011/022051 dated Jul. 24, 2012 (13 pages).

(Continued)

Primary Examiner — Aaron Dunwoody
(74) Attorney, Agent, or Firm — McCormick, Paulding & Huber LLP (57) ABSTRACT A medium connector including a passage configured to allow for the flow of medium, and a multi-portion engagement surface positioned about the passage. The multi-portion engagement surface includes a first surface portion, and a second surface portion. The first surface portion is configured to provide an interference fit with a corresponding sealing surface of a mating connector. The second surface portion is configured to provide a clearance fit with the corresponding sealing surface of the mating connector. The ratio of the first surface portion and the second surface portion is selected to regulate an engagement force between the medium connector and the mating connector.

12 Claims, 5 Drawing Sheets

(56) References Cited

U.S. PATENT DOCUMENTS

| | | | |
|---|---|---|---|
| 4,373,527 A | 2/1983 | Fischell | |
| 4,391,883 A | 7/1983 | Williamson et al. | |
| 4,392,847 A | 7/1983 | Whitney et al. | |
| 4,392,849 A | 7/1983 | Petre et al. | |
| 4,395,259 A | 7/1983 | Prestele et al. | |
| 4,437,859 A | 3/1984 | Whitehouse et al. | |
| 4,443,218 A | 4/1984 | DeCant, Jr. et al. | |
| 4,464,170 A | 8/1984 | Clemens et al. | |
| 4,469,481 A | 9/1984 | Kobayashi | |
| 4,475,901 A | 10/1984 | Kraegen et al. | |
| 4,493,704 A | 1/1985 | Beard et al. | |
| 4,494,950 A | 1/1985 | Fischell | |
| 4,498,843 A | 2/1985 | Schneider et al. | |
| 4,533,346 A | 8/1985 | Cosgrove, Jr. et al. | |
| 4,542,532 A | 9/1985 | McQuilkin | |
| 4,543,093 A | 9/1985 | Christinger | |
| 4,550,731 A | 11/1985 | Batina et al. | |
| 4,559,037 A | 12/1985 | Franetzki et al. | |
| 4,559,038 A | 12/1985 | Berg et al. | |
| 4,562,751 A | 1/1986 | Nason et al. | |
| 4,596,575 A | 6/1986 | Rosenberg et al. | |
| 4,624,661 A | 11/1986 | Arimond | |
| 4,633,878 A | 1/1987 | Bombardieri | |
| 4,648,872 A | 3/1987 | Kamen | |
| 4,673,396 A | 6/1987 | Urbaniak | |
| 4,678,408 A | 7/1987 | Nason et al. | |
| 4,685,903 A | 8/1987 | Cable et al. | |
| 4,690,878 A | 9/1987 | Nakamura | |
| 4,696,671 A | 9/1987 | Epstein et al. | |
| 4,731,051 A | 3/1988 | Fischell | |
| 4,731,726 A | 3/1988 | Allen, III | |
| 4,735,441 A * | 4/1988 | Stephens | 285/148.19 |
| 4,741,731 A | 5/1988 | Starck et al. | |
| 4,743,895 A | 5/1988 | Alexander | |
| 4,747,828 A | 5/1988 | Tseo | |
| 4,790,028 A | 12/1988 | Ramage | |
| 4,803,625 A | 2/1989 | Fu et al. | |
| 4,804,368 A | 2/1989 | Skakoon et al. | |
| 4,809,697 A | 3/1989 | Causey, III et al. | |
| 4,826,810 A | 5/1989 | Aoki | |
| 4,834,712 A | 5/1989 | Quinn et al. | |
| 4,849,852 A | 7/1989 | Mullins | |
| 4,856,340 A | 8/1989 | Garrison | |
| 4,871,351 A | 10/1989 | Feingold | |
| 4,880,712 A | 11/1989 | Gordecki | |
| 4,881,063 A | 11/1989 | Fawcett | |
| 4,898,578 A | 2/1990 | Rubalcaba, Jr. | |
| 4,919,650 A | 4/1990 | Feingold et al. | |
| 4,954,000 A | 9/1990 | Gueret | |
| 4,959,640 A | 9/1990 | Hall | |
| 4,972,508 A | 11/1990 | King | |
| 4,988,337 A | 1/1991 | Ito | |
| 4,997,423 A | 3/1991 | Okuda et al. | |
| 5,009,646 A | 4/1991 | Sudo et al. | |
| 5,019,974 A | 5/1991 | Beckers | |
| 5,034,004 A | 7/1991 | Crankshaw | |
| 5,049,141 A | 9/1991 | Olive | |
| 5,050,612 A | 9/1991 | Matsumura | |
| 5,055,830 A | 10/1991 | Cousins et al. | |
| 5,063,291 A | 11/1991 | Buehring | |
| 5,071,413 A * | 12/1991 | Utterberg | 604/533 |
| 5,078,683 A | 1/1992 | Sancoff et al. | |
| 5,080,653 A | 1/1992 | Voss et al. | |
| 5,088,981 A | 2/1992 | Howson et al. | |
| 5,101,814 A | 4/1992 | Palti | |
| 5,102,388 A | 4/1992 | Richmond | |
| 5,103,216 A | 4/1992 | Sisselman | |
| 5,104,374 A | 4/1992 | Bishko et al. | |
| 5,150,314 A | 9/1992 | Garratt et al. | |
| 5,153,827 A | 10/1992 | Coutréet al. | |
| 5,165,407 A | 11/1992 | Wilson et al. | |
| 5,174,716 A | 12/1992 | Hora et al. | |
| 5,176,502 A | 1/1993 | Sanderson et al. | |
| 5,176,644 A | 1/1993 | Srisathapat et al. | |
| 5,176,662 A | 1/1993 | Bartholomew et al. | |
| 5,181,910 A | 1/1993 | Scanlon | |
| 5,187,746 A | 2/1993 | Narisawa | |
| 5,191,855 A | 3/1993 | Conforti | |
| 5,197,322 A | 3/1993 | Indravudh | |
| 5,197,895 A * | 3/1993 | Stupecky | 439/194 |
| 5,205,819 A | 4/1993 | Ross et al. | |
| 5,216,597 A | 6/1993 | Beckers | |
| 5,217,442 A | 6/1993 | Davis | |
| 5,248,569 A | 9/1993 | Pine et al. | |
| 5,254,093 A | 10/1993 | Bartlett et al. | |
| 5,254,096 A | 10/1993 | Rondelet et al. | |
| 5,257,971 A | 11/1993 | Lord et al. | |
| 5,257,980 A | 11/1993 | Van Antwerp et al. | |
| 5,270,702 A | 12/1993 | Krolak | |
| 5,290,639 A | 3/1994 | Mallory | |
| 5,304,152 A | 4/1994 | Sams | |
| 5,307,263 A | 4/1994 | Brown | |
| 5,314,416 A | 5/1994 | Lewis et al. | |
| 5,317,506 A | 5/1994 | Coutréet al. | |
| 5,337,215 A | 8/1994 | Sunderland et al. | |
| 5,338,157 A | 8/1994 | Blomquist | |
| 5,339,821 A | 8/1994 | Fujimoto | |
| 5,341,291 A | 8/1994 | Roizen et al. | |
| 5,342,324 A | 8/1994 | Tucker | |
| 5,349,852 A | 9/1994 | Kamen et al. | |
| 5,350,411 A | 9/1994 | Ryan et al. | |
| 5,357,427 A | 10/1994 | Langen et al. | |
| 5,364,242 A | 11/1994 | Olsen | |
| 5,364,346 A | 11/1994 | Schrezenmeir | |
| 5,368,562 A | 11/1994 | Blomquist et al. | |
| 5,370,622 A | 12/1994 | Livingston et al. | |
| 5,372,133 A | 12/1994 | Hogen Esch | |
| 5,376,070 A | 12/1994 | Purvis et al. | |
| 5,383,865 A | 1/1995 | Michel | |
| 5,389,078 A | 2/1995 | Zalesky et al. | |
| 5,390,671 A | 2/1995 | Lord et al. | |
| 5,391,157 A | 2/1995 | Harris et al. | |
| 5,399,823 A | 3/1995 | McCusker | |
| 5,403,648 A | 4/1995 | Chan et al. | |
| 5,417,667 A | 5/1995 | Tennican et al. | |
| 5,429,602 A | 7/1995 | Hauser | |
| 5,433,710 A | 7/1995 | VanAntwerp et al. | |
| 5,456,940 A | 10/1995 | Funderburk | |
| 5,460,618 A | 10/1995 | Harreld | |
| 5,462,525 A | 10/1995 | Srisathapat et al. | |
| 5,464,392 A | 11/1995 | Epstein et al. | |
| 5,466,218 A | 11/1995 | Srisathapat et al. | |
| 5,472,317 A | 12/1995 | Field et al. | |
| 5,476,460 A | 12/1995 | Montalvo | |
| 5,478,211 A | 12/1995 | Dominiak et al. | |
| 5,482,446 A | 1/1996 | Williamson et al. | |
| 5,497,772 A | 3/1996 | Schulman et al. | |
| 5,505,709 A | 4/1996 | Funderburk et al. | |
| 5,507,727 A | 4/1996 | Crainich | |
| 5,508,690 A | 4/1996 | Shur et al. | |
| 5,514,097 A | 5/1996 | Knauer | |
| 5,514,103 A | 5/1996 | Srisathapat et al. | |
| 5,522,803 A | 6/1996 | Teissen-Simony | |
| 5,526,844 A | 6/1996 | Kamen et al. | |
| 5,527,307 A | 6/1996 | Srisathapat et al. | |
| 5,528,359 A | 6/1996 | Taguchi | |
| 5,531,697 A | 7/1996 | Olsen et al. | |
| 5,531,698 A | 7/1996 | Olsen | |
| 5,533,389 A | 7/1996 | Kamen et al. | |
| 5,533,996 A | 7/1996 | Murphey et al. | |
| 5,538,399 A | 7/1996 | Johnson | |
| 5,540,564 A | 7/1996 | Klopfer | |
| 5,543,588 A | 8/1996 | Bisset et al. | |
| 5,545,140 A | 8/1996 | Conero et al. | |
| 5,545,142 A | 8/1996 | Stephens et al. | |
| 5,545,143 A | 8/1996 | Fischell | |
| 5,545,152 A | 8/1996 | Funderburk et al. | |
| 5,558,640 A | 9/1996 | Pfeiler et al. | |
| 5,558,641 A | 9/1996 | Glantz et al. | |
| 5,562,618 A | 10/1996 | Cai et al. | |
| 5,564,915 A | 10/1996 | Johnson | |
| 5,567,119 A | 10/1996 | Johnson | |
| 5,567,136 A | 10/1996 | Johnson | |
| 5,569,026 A | 10/1996 | Novak | |

(56) References Cited

U.S. PATENT DOCUMENTS

| | | |
|---|---|---|
| 5,569,186 A | 10/1996 | Lord et al. |
| 5,569,187 A | 10/1996 | Kaiser |
| 5,573,506 A | 11/1996 | Vasko |
| 5,575,310 A | 11/1996 | Kamen et al. |
| 5,582,593 A | 12/1996 | Hultman |
| 5,584,813 A | 12/1996 | Livingston et al. |
| 5,593,390 A | 1/1997 | Castellano et al. |
| 5,594,638 A | 1/1997 | Iliff |
| 5,609,060 A | 3/1997 | Dent |
| 5,609,575 A | 3/1997 | Larson et al. |
| 5,613,945 A | 3/1997 | Cai et al. |
| 5,620,312 A | 4/1997 | Hyman et al. |
| 5,626,144 A | 5/1997 | Tacklind et al. |
| 5,630,710 A | 5/1997 | Tune et al. |
| 5,632,315 A * | 5/1997 | Rose ............................ 141/329 |
| 5,632,729 A | 5/1997 | Cai et al. |
| 5,637,095 A | 6/1997 | Nason et al. |
| 5,637,420 A | 6/1997 | Jones, Jr. et al. |
| 5,641,892 A | 6/1997 | Larkins et al. |
| 5,643,212 A | 7/1997 | Coutré et al. |
| 5,647,853 A | 7/1997 | Feldmann et al. |
| 5,647,854 A | 7/1997 | Olsen et al. |
| 5,651,775 A | 7/1997 | Walker et al. |
| 5,658,133 A | 8/1997 | Anderson et al. |
| 5,658,250 A | 8/1997 | Blomquist et al. |
| 5,658,252 A | 8/1997 | Johnson |
| 5,660,176 A | 8/1997 | Iliff |
| 5,665,065 A | 9/1997 | Colman et al. |
| 5,669,877 A | 9/1997 | Blomquist |
| 5,669,887 A | 9/1997 | Cooper |
| 5,678,568 A | 10/1997 | Uchikubo et al. |
| 5,681,285 A | 10/1997 | Ford et al. |
| 5,685,844 A | 11/1997 | Marttila |
| 5,687,734 A | 11/1997 | Dempsey et al. |
| 5,695,473 A | 12/1997 | Olsen |
| 5,704,366 A | 1/1998 | Tacklind et al. |
| 5,713,856 A | 2/1998 | Eggers et al. |
| 5,713,857 A | 2/1998 | Grimard et al. |
| 5,716,725 A | 2/1998 | Riveron et al. |
| 5,718,562 A | 2/1998 | Lawless et al. |
| 5,720,729 A | 2/1998 | Kriesel |
| 5,727,241 A | 3/1998 | Yamano et al. |
| 5,733,673 A | 3/1998 | Kunert |
| 5,743,873 A | 4/1998 | Cai et al. |
| 5,752,940 A | 5/1998 | Grimard |
| 5,755,744 A | 5/1998 | Shaw et al. |
| 5,762,632 A | 6/1998 | Whisson |
| 5,764,159 A | 6/1998 | Neftel |
| 5,772,409 A | 6/1998 | Johnson |
| 5,772,635 A | 6/1998 | Dastur et al. |
| 5,776,116 A | 7/1998 | Lopez et al. |
| 5,779,665 A | 7/1998 | Mastrototaro et al. |
| 5,785,681 A | 7/1998 | Indravudh |
| 5,788,669 A | 8/1998 | Peterson |
| 5,788,671 A | 8/1998 | Johnson |
| 5,788,673 A | 8/1998 | Young et al. |
| 5,788,678 A | 8/1998 | Van Antwerp |
| 5,795,337 A | 8/1998 | Grimard |
| 5,800,387 A | 9/1998 | Duffy et al. |
| 5,800,420 A | 9/1998 | Gross et al. |
| 5,801,600 A | 9/1998 | Butland et al. |
| 5,807,336 A | 9/1998 | Russo et al. |
| 5,810,001 A | 9/1998 | Genga et al. |
| 5,810,771 A | 9/1998 | Blomquist |
| 5,814,015 A | 9/1998 | Gargano et al. |
| 5,822,715 A | 10/1998 | Worthington et al. |
| 5,823,746 A | 10/1998 | Johnson |
| 5,832,448 A | 11/1998 | Brown |
| 5,840,020 A | 11/1998 | Heinonen et al. |
| 5,840,026 A | 11/1998 | Uber, III et al. |
| 5,843,146 A | 12/1998 | Cross, Jr. |
| 5,851,197 A | 12/1998 | Marano et al. |
| 5,851,692 A | 12/1998 | Potts |
| 5,861,018 A | 1/1999 | Feierbach |
| 5,868,669 A | 2/1999 | Iliff |
| 5,871,465 A | 2/1999 | Vasko |
| 5,876,370 A | 3/1999 | Blomquist |
| 5,879,143 A | 3/1999 | Cote et al. |
| 5,879,144 A | 3/1999 | Johnson |
| 5,879,163 A | 3/1999 | Brown et al. |
| 5,882,256 A | 3/1999 | Shropshire |
| 5,885,245 A | 3/1999 | Lynch et al. |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,925,021 A | 7/1999 | Castellano et al. |
| 5,928,196 A | 7/1999 | Johnson et al. |
| 5,928,202 A | 7/1999 | Linnebjerg |
| 5,931,791 A | 8/1999 | Saltzstein et al. |
| 5,933,136 A | 8/1999 | Brown |
| 5,935,099 A | 8/1999 | Peterson et al. |
| 5,935,105 A | 8/1999 | Manning et al. |
| 5,935,106 A | 8/1999 | Olsen |
| 5,940,801 A | 8/1999 | Brown |
| 5,951,521 A | 9/1999 | Mastrototaro et al. |
| 5,954,485 A | 9/1999 | Johnson et al. |
| 5,954,697 A | 9/1999 | Srisathapat et al. |
| 5,954,700 A | 9/1999 | Kovelman |
| 5,956,501 A | 9/1999 | Brown |
| 5,957,890 A | 9/1999 | Mann et al. |
| 5,960,403 A | 9/1999 | Brown |
| 5,968,011 A | 10/1999 | Larsen et al. |
| 5,971,963 A | 10/1999 | Choi |
| 5,973,623 A | 10/1999 | Gupta et al. |
| 5,980,506 A | 11/1999 | Mathiasen |
| 5,989,216 A | 11/1999 | Johnson et al. |
| 5,989,227 A | 11/1999 | Vetter et al. |
| 5,997,476 A | 12/1999 | Brown |
| 6,007,941 A | 12/1999 | Hermann et al. |
| 6,009,339 A | 12/1999 | Bentsen et al. |
| 6,014,587 A | 1/2000 | Shaw et al. |
| 6,017,326 A | 1/2000 | Pasqualucci et al. |
| 6,017,328 A | 1/2000 | Fischell et al. |
| 6,024,539 A | 2/2000 | Blomquist |
| 6,032,119 A | 2/2000 | Brown et al. |
| 6,042,565 A | 3/2000 | Hirschman et al. |
| 6,056,522 A | 5/2000 | Johnson |
| 6,056,718 A | 5/2000 | Funderburk et al. |
| 6,059,753 A | 5/2000 | Faust et al. |
| 6,063,059 A | 5/2000 | Kriesel |
| 6,073,036 A | 6/2000 | Heikkinen et al. |
| 6,077,055 A | 6/2000 | Vilks |
| 6,086,575 A | 7/2000 | Mejslov |
| 6,090,071 A | 7/2000 | Kriesel |
| 6,090,081 A | 7/2000 | Sudo et al. |
| 6,093,172 A | 7/2000 | Funderburk et al. |
| 6,096,011 A | 8/2000 | Trombley, III et al. |
| 6,099,507 A | 8/2000 | Heinzerling |
| 6,101,478 A | 8/2000 | Brown |
| 6,110,152 A | 8/2000 | Kovelman |
| 6,112,111 A | 8/2000 | Glantz |
| 6,123,686 A | 9/2000 | Olsen et al. |
| 6,123,690 A | 9/2000 | Mejslov |
| 6,135,949 A | 10/2000 | Russo et al. |
| 6,142,150 A | 11/2000 | O'Mahoney |
| 6,165,154 A | 12/2000 | Gray et al. |
| 6,171,287 B1 | 1/2001 | Lynn et al. |
| 6,202,708 B1 | 3/2001 | Bynum |
| 6,206,856 B1 | 3/2001 | Mahurkar |
| 6,211,856 B1 | 4/2001 | Choi et al. |
| 6,216,695 B1 | 4/2001 | Buchl |
| 6,217,550 B1 * | 4/2001 | Capes ............................ 604/110 |
| 6,225,711 B1 | 5/2001 | Gupta et al. |
| 6,241,704 B1 | 6/2001 | Peterson et al. |
| 6,246,992 B1 | 6/2001 | Brown |
| 6,248,093 B1 | 6/2001 | Moberg |
| 6,253,804 B1 | 7/2001 | Safabash |
| 6,254,586 B1 | 7/2001 | Mann et al. |
| 6,259,587 B1 | 7/2001 | Sheldon et al. |
| 6,267,564 B1 | 7/2001 | Rapheal |
| 6,269,340 B1 | 7/2001 | Ford et al. |
| 6,270,455 B1 | 8/2001 | Brown |
| 6,280,416 B1 | 8/2001 | Van Antwerp et al. |

(56) References Cited

U.S. PATENT DOCUMENTS

| | | | |
|---|---|---|---|
| 6,283,943 B1 | 9/2001 | Dy et al. |
| 6,293,159 B1 | 9/2001 | Kriesel et al. |
| 6,293,925 B1 | 9/2001 | Safabash et al. |
| 6,305,908 B1 | 10/2001 | Hermann et al. |
| 6,309,375 B1 | 10/2001 | Glines et al. |
| 6,311,868 B1 | 11/2001 | Krietemeier et al. |
| 6,321,158 B1 | 11/2001 | DeLorme et al. |
| 6,362,591 B1 | 3/2002 | Moberg |
| 6,364,859 B1 | 4/2002 | St. Romain et al. |
| 6,364,865 B1 | 4/2002 | Lavi et al. |
| 6,374,876 B2 | 4/2002 | Bynum |
| 6,375,638 B2 | 4/2002 | Nason et al. |
| 6,416,293 B1 | 7/2002 | Bouchard et al. |
| 6,422,057 B1 | 7/2002 | Anderson |
| 6,423,035 B1 | 7/2002 | Das et al. |
| 6,427,088 B1 | 7/2002 | Bowman, IV et al. |
| 6,428,509 B1 | 8/2002 | Fielder |
| 6,447,481 B1 | 9/2002 | Duchon et al. |
| 6,453,956 B2 | 9/2002 | Safabash |
| 6,458,102 B1 | 10/2002 | Mann et al. |
| 6,459,424 B1 | 10/2002 | Resman |
| 6,461,329 B1 | 10/2002 | Van Antwerp et al. |
| 6,461,331 B1 | 10/2002 | Van Antwerp |
| 6,466,203 B2 | 10/2002 | Van Ee |
| 6,475,180 B2 | 11/2002 | Peterson et al. |
| 6,475,196 B1 | 11/2002 | Vachon |
| 6,485,461 B1 | 11/2002 | Mason et al. |
| 6,485,465 B2 | 11/2002 | Moberg et al. |
| 6,520,938 B1 | 2/2003 | Funderburk et al. |
| 6,537,268 B1 | 3/2003 | Gibson et al. |
| 6,549,423 B1 | 4/2003 | Brodnick |
| 6,551,276 B1 | 4/2003 | Mann et al. |
| 6,551,277 B1 | 4/2003 | Ford |
| 6,554,798 B1 | 4/2003 | Mann et al. |
| 6,554,800 B1 | 4/2003 | Nezhadian et al. |
| 6,555,986 B2 | 4/2003 | Moberg |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,023 B1 | 5/2003 | Marrs et al. |
| 6,564,105 B2 | 5/2003 | Starkweather et al. |
| 6,571,128 B2 | 5/2003 | Lebel et al. |
| 6,572,542 B1 | 6/2003 | Houben et al. |
| 6,572,586 B1 | 6/2003 | Wojcik |
| 6,577,899 B2 | 6/2003 | Lebel et al. |
| RE38,189 E | 7/2003 | Walker et al. |
| 6,585,644 B2 | 7/2003 | Lebel et al. |
| 6,585,695 B1 | 7/2003 | Adair et al. |
| 6,591,876 B2 | 7/2003 | Safabash |
| 6,592,551 B1 | 7/2003 | Cobb |
| 6,595,756 B2 | 7/2003 | Gray et al. |
| 6,607,509 B2 | 8/2003 | Bobroff et al. |
| 6,613,015 B2 | 9/2003 | Sandstrom et al. |
| D480,477 S | 10/2003 | Bush et al. |
| 6,641,533 B2 | 11/2003 | Causey, III et al. |
| 6,642,936 B1 | 11/2003 | Engholm et al. |
| 6,645,177 B1 | 11/2003 | Shearn |
| 6,648,821 B2 | 11/2003 | Lebel et al. |
| 6,652,493 B1 | 11/2003 | Das |
| 6,652,510 B2 | 11/2003 | Lord et al. |
| 6,656,148 B2 | 12/2003 | Das et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,665,909 B2 | 12/2003 | Collins et al. |
| 6,666,839 B2 * | 12/2003 | Utterberg et al. ............ 604/5.01 |
| 6,669,669 B2 | 12/2003 | Flaherty et al. |
| 6,684,058 B1 | 1/2004 | Karacaoglu et al. |
| 6,685,678 B2 | 2/2004 | Evans et al. |
| 6,687,546 B2 | 2/2004 | Lebel et al. |
| 6,689,091 B2 | 2/2004 | Bui et al. |
| 6,691,043 B2 | 2/2004 | Ribeiro, Jr. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,704,034 B1 | 3/2004 | Rodriguez et al. |
| 6,716,195 B2 | 4/2004 | Nolan, Jr. et al. |
| 6,723,072 B2 | 4/2004 | Flaherty et al. |
| 6,733,446 B2 | 5/2004 | Lebel et al. |
| 6,740,059 B2 | 5/2004 | Flaherty |
| 6,740,072 B2 | 5/2004 | Starkweather et al. |
| 6,740,075 B2 | 5/2004 | Lebel et al. |
| 6,743,205 B2 | 6/2004 | Nolan, Jr. et al. |
| 6,744,350 B2 | 6/2004 | Blomquist |
| 6,749,586 B2 | 6/2004 | Vasko |
| 6,749,587 B2 | 6/2004 | Flaherty |
| 6,752,299 B2 | 6/2004 | Shetler et al. |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,770,067 B2 | 8/2004 | Lorenzen et al. |
| 6,772,650 B2 | 8/2004 | Ohyama et al. |
| 6,800,071 B1 | 10/2004 | McConnell et al. |
| 6,801,420 B2 | 10/2004 | Talbot et al. |
| 6,805,693 B2 | 10/2004 | Gray et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,817,990 B2 | 11/2004 | Yap et al. |
| 6,827,702 B2 | 12/2004 | Lebel et al. |
| 6,830,558 B2 | 12/2004 | Flaherty et al. |
| 6,835,190 B2 | 12/2004 | Nguyen |
| 6,845,465 B2 | 1/2005 | Hashemi |
| 6,852,104 B2 | 2/2005 | Blomquist |
| 6,854,620 B2 | 2/2005 | Ramey |
| 6,872,200 B2 | 3/2005 | Mann et al. |
| 6,873,268 B2 | 3/2005 | Lebel et al. |
| 6,879,930 B2 | 4/2005 | Sinclair et al. |
| 6,892,998 B2 * | 5/2005 | Newton ..................... 251/149.1 |
| 6,902,207 B2 | 6/2005 | Lickliter |
| 6,916,010 B2 | 7/2005 | Beck et al. |
| 6,930,602 B2 | 8/2005 | Villaseca et al. |
| 6,932,584 B2 | 8/2005 | Gray et al. |
| 6,936,029 B2 | 8/2005 | Mann et al. |
| 6,945,760 B2 | 9/2005 | Gray et al. |
| 6,950,708 B2 | 9/2005 | Bowman, IV et al. |
| 6,951,551 B2 | 10/2005 | Hudon |
| 6,958,705 B2 | 10/2005 | Lebel et al. |
| 6,960,192 B1 | 11/2005 | Flaherty et al. |
| 6,960,195 B2 | 11/2005 | Heinz et al. |
| 6,964,643 B2 | 11/2005 | Hovland et al. |
| 6,974,437 B2 | 12/2005 | Lebel et al. |
| 6,978,517 B2 | 12/2005 | Collins et al. |
| 6,979,326 B2 | 12/2005 | Mann et al. |
| 6,994,619 B2 | 2/2006 | Scholten |
| 6,997,905 B2 | 2/2006 | Gillespie, Jr. et al. |
| 6,997,907 B2 | 2/2006 | Safabash et al. |
| 6,997,910 B2 | 2/2006 | Howlett et al. |
| 6,997,920 B2 | 2/2006 | Mann et al. |
| 6,997,921 B2 | 2/2006 | Gray et al. |
| 6,999,854 B2 | 2/2006 | Roth |
| 7,011,608 B2 | 3/2006 | Spencer |
| 7,018,360 B2 | 3/2006 | Flaherty et al. |
| 7,021,560 B2 | 4/2006 | Gray et al. |
| 7,024,245 B2 | 4/2006 | Lebel et al. |
| 7,025,226 B2 | 4/2006 | Ramey |
| 7,025,743 B2 | 4/2006 | Mann et al. |
| 7,029,455 B2 | 4/2006 | Flaherty |
| 7,029,456 B2 | 4/2006 | Ware et al. |
| 7,033,338 B2 | 4/2006 | Vilks et al. |
| 7,033,339 B1 | 4/2006 | Lynn |
| 7,041,082 B2 | 5/2006 | Blomquist et al. |
| 7,044,937 B1 * | 5/2006 | Kirwan et al. ................. 604/264 |
| 7,045,361 B2 | 5/2006 | Heiss et al. |
| 7,046,230 B2 | 5/2006 | Zadesky et al. |
| 7,050,927 B2 | 5/2006 | Sinclair et al. |
| 7,052,251 B2 | 5/2006 | Nason et al. |
| 7,052,483 B2 | 5/2006 | Wojcik |
| 7,061,140 B2 | 6/2006 | Zhang et al. |
| 7,063,684 B2 | 6/2006 | Moberg |
| 7,066,029 B2 | 6/2006 | Beavis et al. |
| 7,074,209 B2 | 7/2006 | Evans et al. |

(56) References Cited

U.S. PATENT DOCUMENTS

| | | |
|---|---|---|
| 7,075,512 B1 | 7/2006 | Fabre et al. |
| 7,098,803 B2 | 8/2006 | Mann et al. |
| 7,101,509 B2 * | 9/2006 | Chang et al. ................. 422/68.1 |
| 7,109,878 B2 | 9/2006 | Mann et al. |
| 7,115,113 B2 | 10/2006 | Evans et al. |
| 7,131,967 B2 | 11/2006 | Gray et al. |
| 7,137,964 B2 | 11/2006 | Flaherty |
| 7,144,384 B2 | 12/2006 | Gorman et al. |
| 7,146,977 B2 | 12/2006 | Beavis et al. |
| 7,278,983 B2 | 10/2007 | Ireland et al. |
| 7,303,549 B2 | 12/2007 | Flaherty et al. |
| 7,305,984 B2 | 12/2007 | Altobelli et al. |
| 7,306,578 B2 | 12/2007 | Gray et al. |
| 7,342,660 B2 | 3/2008 | Altobelli et al. |
| 7,390,314 B2 | 6/2008 | Stutz, Jr. et al. |
| 7,498,563 B2 | 3/2009 | Mandro et al. |
| 7,534,231 B2 * | 5/2009 | Kuracina et al. ............. 604/192 |
| 7,559,530 B2 * | 7/2009 | Korogi et al. ............. 251/149.6 |
| 7,682,338 B2 | 3/2010 | Griffin |
| 7,717,881 B2 * | 5/2010 | Caizza et al. ................. 604/240 |
| 7,785,296 B2 * | 8/2010 | Muskatello et al. .......... 604/192 |
| 7,806,868 B2 | 10/2010 | De Polo et al. |
| 7,914,502 B2 * | 3/2011 | Newton et al. ................. 604/247 |
| 7,926,856 B2 * | 4/2011 | Smutney et al. ............. 285/330 |
| 7,927,314 B2 * | 4/2011 | Kuracina et al. ............. 604/192 |
| 8,016,789 B2 | 9/2011 | Grant et al. |
| 8,034,026 B2 | 10/2011 | Grant et al. |
| 8,262,616 B2 | 9/2012 | Grant et al. |
| 2001/0031944 A1 | 10/2001 | Peterson et al. |
| 2001/0034502 A1 | 10/2001 | Moberg et al. |
| 2001/0041869 A1 | 11/2001 | Causey, III et al. |
| 2001/0056258 A1 | 12/2001 | Evans |
| 2002/0002326 A1 | 1/2002 | Causey, III et al. |
| 2002/0013613 A1 | 1/2002 | Haller et al. |
| 2002/0022807 A1 | 2/2002 | Duchon et al. |
| 2002/0038392 A1 | 3/2002 | De La Huerga |
| 2002/0043951 A1 | 4/2002 | Moberg |
| 2002/0052539 A1 | 5/2002 | Haller et al. |
| 2002/0052574 A1 | 5/2002 | Hochman et al. |
| 2002/0056114 A1 | 5/2002 | Fillebrown et al. |
| 2002/0077598 A1 | 6/2002 | Yap et al. |
| 2002/0077852 A1 | 6/2002 | Ford et al. |
| 2002/0082665 A1 | 6/2002 | Haller et al. |
| 2002/0091454 A1 | 7/2002 | Vasko |
| 2002/0107481 A1 | 8/2002 | Reilly et al. |
| 2002/0123672 A1 | 9/2002 | Christophersom et al. |
| 2002/0126036 A1 | 9/2002 | Flaherty et al. |
| 2002/0143290 A1 | 10/2002 | Bui et al. |
| 2002/0158838 A1 | 10/2002 | Smith et al. |
| 2002/0169439 A1 | 11/2002 | Flaherty |
| 2002/0173748 A1 | 11/2002 | McConnell et al. |
| 2002/0193679 A1 | 12/2002 | Malave et al. |
| 2002/0193846 A1 | 12/2002 | Pool et al. |
| 2003/0009133 A1 | 1/2003 | Ramey |
| 2003/0014013 A1 | 1/2003 | Choi |
| 2003/0028079 A1 | 2/2003 | Lebel et al. |
| 2003/0028346 A1 | 2/2003 | Sinclair et al. |
| 2003/0065308 A1 | 4/2003 | Lebel et al. |
| 2003/0069543 A1 | 4/2003 | Carpenter et al. |
| 2003/0076306 A1 | 4/2003 | Zadesky et al. |
| 2003/0088238 A1 | 5/2003 | Poulsen et al. |
| 2003/0114836 A1 | 6/2003 | Estes et al. |
| 2003/0125672 A1 | 7/2003 | Adair et al. |
| 2003/0130618 A1 | 7/2003 | Gray et al. |
| 2003/0132922 A1 | 7/2003 | Philipp |
| 2003/0141981 A1 | 7/2003 | Bul et al. |
| 2003/0161744 A1 | 8/2003 | Vilks et al. |
| 2003/0163089 A1 | 8/2003 | Bynum |
| 2003/0163090 A1 | 8/2003 | Blomquist et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0212364 A1 | 11/2003 | Mann et al. |
| 2003/0212379 A1 | 11/2003 | Bylund et al. |
| 2003/0229311 A1 | 12/2003 | Morris et al. |
| 2003/0233069 A1 | 12/2003 | Gillespie, Jr. et al. |
| 2004/0003493 A1 | 1/2004 | Adair et al. |
| 2004/0054326 A1 | 3/2004 | Hommann et al. |
| 2004/0059315 A1 | 3/2004 | Erickson et al. |
| 2004/0064088 A1 | 4/2004 | Gorman et al. |
| 2004/0068230 A1 | 4/2004 | Estes et al. |
| 2004/0073095 A1 | 4/2004 | Causey, III et al. |
| 2004/0073161 A1 | 4/2004 | Tachibana |
| 2004/0082908 A1 | 4/2004 | Whitehurst et al. |
| 2004/0082918 A1 | 4/2004 | Evans et al. |
| 2004/0085215 A1 | 5/2004 | Moberg et al. |
| 2004/0092873 A1 | 5/2004 | Moberg |
| 2004/0092878 A1 | 5/2004 | Flaherty |
| 2004/0116893 A1 | 6/2004 | Spohn et al. |
| 2004/0121767 A1 | 6/2004 | Simpson et al. |
| 2004/0127958 A1 | 7/2004 | Mazar et al. |
| 2004/0133166 A1 | 7/2004 | Moberg et al. |
| 2004/0135078 A1 | 7/2004 | Mandro et al. |
| 2004/0140304 A1 | 7/2004 | Leyendecker |
| 2004/0158193 A1 | 8/2004 | Bui et al. |
| 2004/0162528 A1 | 8/2004 | Horvath et al. |
| 2004/0167464 A1 | 8/2004 | Ireland et al. |
| 2004/0172301 A1 | 9/2004 | Mihai et al. |
| 2004/0176667 A1 | 9/2004 | Mihai et al. |
| 2004/0176725 A1 | 9/2004 | Stutz, Jr. et al. |
| 2004/0193090 A1 | 9/2004 | Lebel et al. |
| 2004/0207404 A1 | 10/2004 | Zhang et al. |
| 2004/0235446 A1 | 11/2004 | Flaherty et al. |
| 2004/0243065 A1 | 12/2004 | McConnell et al. |
| 2005/0015056 A1 | 1/2005 | Duchon et al. |
| 2005/0021000 A1 | 1/2005 | Adair et al. |
| 2005/0022274 A1 | 1/2005 | Campbell et al. |
| 2005/0027254 A1 | 2/2005 | Vasko |
| 2005/0035956 A1 | 2/2005 | Sinclair et al. |
| 2005/0048900 A1 | 3/2005 | Scholten |
| 2005/0052429 A1 | 3/2005 | Philipp |
| 2005/0055242 A1 | 3/2005 | Bello et al. |
| 2005/0055244 A1 | 3/2005 | Mullan et al. |
| 2005/0062732 A1 | 3/2005 | Sinclair et al. |
| 2005/0063857 A1 | 3/2005 | Alheidt et al. |
| 2005/0065464 A1 | 3/2005 | Talbot et al. |
| 2005/0065817 A1 | 3/2005 | Mihai et al. |
| 2005/0069425 A1 | 3/2005 | Gray et al. |
| 2005/0085760 A1 | 4/2005 | Ware et al. |
| 2005/0096593 A1 | 5/2005 | Pope et al. |
| 2005/0137530 A1 | 6/2005 | Campbell et al. |
| 2005/0137573 A1 | 6/2005 | McLaughlin |
| 2005/0148938 A1 | 7/2005 | Blomquist |
| 2005/0171512 A1 | 8/2005 | Flaherty |
| 2005/0171513 A1 | 8/2005 | Mann et al. |
| 2005/0177111 A1 | 8/2005 | Ozeri et al. |
| 2005/0182366 A1 | 8/2005 | Vogt et al. |
| 2005/0182383 A1 | 8/2005 | LaPorte et al. |
| 2005/0187515 A1 | 8/2005 | Varrichio et al. |
| 2005/0187593 A1 | 8/2005 | Housworth et al. |
| 2005/0192494 A1 | 9/2005 | Ginsberg |
| 2005/0203461 A1 | 9/2005 | Flaherty et al. |
| 2005/0215982 A1 | 9/2005 | Malave et al. |
| 2005/0224705 A1 | 10/2005 | Tobiason et al. |
| 2005/0234404 A1 | 10/2005 | Vilks et al. |
| 2005/0238503 A1 | 10/2005 | Rush et al. |
| 2005/0238507 A1 | 10/2005 | Dilanni et al. |
| 2005/0245904 A1 | 11/2005 | Estes et al. |
| 2005/0250368 A1 | 11/2005 | Singer et al. |
| 2005/0261660 A1 | 11/2005 | Choi |
| 2005/0263615 A1 | 12/2005 | Kriesel et al. |
| 2005/0267363 A1 | 12/2005 | Duchon et al. |
| 2005/0267550 A1 | 12/2005 | Hess et al. |
| 2005/0267928 A1 | 12/2005 | Anderson et al. |
| 2005/0273059 A1 | 12/2005 | Mernoe et al. |
| 2005/0285880 A1 | 12/2005 | Lai et al. |
| 2006/0016800 A1 | 1/2006 | Paradiso et al. |
| 2006/0025663 A1 | 2/2006 | Talbot et al. |
| 2006/0026535 A1 | 2/2006 | Hotelling et al. |
| 2006/0026536 A1 | 2/2006 | Hotelling et al. |
| 2006/0038791 A1 | 2/2006 | Mackey |
| 2006/0041229 A1 | 2/2006 | Garibotto et al. |
| 2006/0065772 A1 | 3/2006 | Grant et al. |
| 2006/0066581 A1 | 3/2006 | Lyon et al. |

(56) References Cited

U.S. PATENT DOCUMENTS

| | | |
|---|---|---|
| 2006/0097991 A1 | 5/2006 | Hotelling et al. |
| 2006/0100591 A1 | 5/2006 | Alheidt et al. |
| 2006/0106346 A1 | 5/2006 | Sullivan et al. |
| 2006/0123884 A1 | 6/2006 | Selker et al. |
| 2006/0129112 A1 | 6/2006 | Lynn |
| 2006/0144942 A1 | 7/2006 | Evans et al. |
| 2006/0160670 A1 | 7/2006 | Spencer |
| 2006/0161870 A1 | 7/2006 | Hotelling et al. |
| 2006/0161871 A1 | 7/2006 | Hotelling et al. |
| 2006/0173406 A1 | 8/2006 | Hayes et al. |
| 2006/0173444 A1 | 8/2006 | Choy et al. |
| 2006/0178633 A1 | 8/2006 | Garibotto et al. |
| 2006/0178836 A1 | 8/2006 | Bai et al. |
| 2006/0184084 A1 | 8/2006 | Ware et al. |
| 2006/0184123 A1 | 8/2006 | Gillespie, Jr. et al. |
| 2006/0184154 A1 | 8/2006 | Moberg et al. |
| 2006/0200257 A1 | 9/2006 | Kirste et al. |
| 2006/0227117 A1 | 10/2006 | Proctor |
| 2006/0229557 A1 | 10/2006 | Fathallah et al. |
| 2006/0232554 A1 | 10/2006 | Wong et al. |
| 2006/0236262 A1 | 10/2006 | Bathiche et al. |
| 2006/0236263 A1 | 10/2006 | Bathiche et al. |
| 2006/0253085 A1 | 11/2006 | Geismar et al. |
| 2006/0264894 A1 | 11/2006 | Moberg et al. |
| 2006/0282290 A1 | 12/2006 | Flaherty et al. |
| 2007/0049870 A1 | 3/2007 | Gray et al. |
| 2007/0060872 A1 | 3/2007 | Hall et al. |
| 2007/0062250 A1 | 3/2007 | Krulevitch et al. |
| 2007/0066940 A1 | 3/2007 | Karunaratne et al. |
| 2007/0066956 A1 | 3/2007 | Finkel |
| 2007/0072146 A1 | 3/2007 | Pierson |
| 2007/0093750 A1 | 4/2007 | Jan et al. |
| 2007/0100283 A1 | 5/2007 | Causey, III et al. |
| 2007/0112298 A1 | 5/2007 | Mueller, Jr. et al. |
| 2007/0118405 A1 | 5/2007 | Campbell et al. |
| 2007/0161955 A1 | 7/2007 | Bynum et al. |
| 2007/0167905 A1 | 7/2007 | Estes et al. |
| 2007/0178776 A1 | 8/2007 | Etter et al. |
| 2007/0191770 A1 | 8/2007 | Moberg et al. |
| 2007/0203439 A1 | 8/2007 | Boyd et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |
| 2007/0255250 A1 | 11/2007 | Moberg et al. |
| 2007/0258395 A1 | 11/2007 | Jollota et al. |
| 2008/0009824 A1 | 1/2008 | Moberg et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0097321 A1 | 4/2008 | Mounce et al. |
| 2008/0097327 A1 | 4/2008 | Bente et al. |
| 2008/0097328 A1 | 4/2008 | Moberg et al. |
| 2008/0097381 A1 | 4/2008 | Moberg et al. |
| 2008/0125700 A1 | 5/2008 | Moberg et al. |
| 2008/0125701 A1 | 5/2008 | Moberg et al. |
| 2008/0160492 A1 | 7/2008 | Campbell et al. |
| 2008/0161754 A1 | 7/2008 | Marano-Ford |
| 2008/0177900 A1 | 7/2008 | Grant et al. |
| 2008/0243079 A1 | 10/2008 | Wooley et al. |
| 2008/0255502 A1 | 10/2008 | Jacobson et al. |
| 2008/0294108 A1 | 11/2008 | Briones et al. |
| 2009/0036870 A1 | 2/2009 | Mounce et al. |
| 2009/0062767 A1 | 3/2009 | Van Antwerp et al. |
| 2009/0062778 A1 | 3/2009 | Bengtsson et al. |
| 2009/0069749 A1 | 3/2009 | Miller et al. |
| 2009/0076461 A1 | 3/2009 | Susi et al. |
| 2009/0099523 A1 | 4/2009 | Grant et al. |
| 2009/0143735 A1 | 6/2009 | De Polo et al. |
| 2009/0160654 A1 | 6/2009 | Yang |
| 2009/0163855 A1 | 6/2009 | Shin et al. |
| 2009/0164251 A1 | 6/2009 | Hayter |
| 2009/0171291 A1 | 7/2009 | Bente, IV et al. |
| 2009/0234213 A1 | 9/2009 | Hayes et al. |
| 2009/0254025 A1 | 10/2009 | Simmons |
| 2009/0259217 A1 | 10/2009 | Hyde et al. |
| 2009/0270811 A1 | 10/2009 | Mounce et al. |
| 2010/0063445 A1 | 3/2010 | Sternberg et al. |
| 2010/0186739 A1 | 7/2010 | Kronestedt et al. |
| 2010/0305512 A1 | 12/2010 | Guillermo et al. |
| 2011/0208123 A1 | 8/2011 | Gray et al. |

FOREIGN PATENT DOCUMENTS

| | | |
|---|---|---|
| DE | 20110059 A1 | 8/2002 |
| EP | 0256694 A1 | 2/1988 |
| EP | 0258566 A2 | 3/1988 |
| EP | 0338671 A1 | 10/1989 |
| EP | 0398394 A2 | 11/1990 |
| EP | 0554995 B1 | 8/1993 |
| EP | 0749757 A2 | 12/1996 |
| EP | 0763368 A2 | 3/1997 |
| EP | 0806738 A1 | 11/1997 |
| EP | 0830597 B1 | 3/1998 |
| EP | 0917882 A1 | 5/1999 |
| EP | 1007137 B1 | 6/2000 |
| EP | 1109586 B1 | 6/2001 |
| EP | 1177802 A1 | 2/2002 |
| EP | 1338295 A1 | 8/2003 |
| EP | 1473050 A1 | 3/2004 |
| EP | 1115435 B1 | 8/2005 |
| EP | 1347705 B1 | 12/2005 |
| EP | 1688085 A1 | 8/2006 |
| EP | 1839694 A1 | 10/2007 |
| GB | 2218831 A | 11/1989 |
| WO | 94/08647 A1 | 4/1994 |
| WO | 95/24229 A2 | 9/1995 |
| WO | 95/28878 A1 | 11/1995 |
| WO | 95/31233 A1 | 11/1995 |
| WO | 96/08281 A1 | 3/1996 |
| WO | 96/14100 A1 | 5/1996 |
| WO | 96/20745 A1 | 7/1996 |
| WO | 96/36389 A1 | 11/1996 |
| WO | 97/21456 A1 | 6/1997 |
| WO | 97/40482 A1 | 10/1997 |
| WO | 98/14234 A1 | 4/1998 |
| WO | 98/17336 A1 | 4/1998 |
| WO | 98/20439 A1 | 5/1998 |
| WO | 98/24358 A2 | 6/1998 |
| WO | 98/42407 A1 | 10/1998 |
| WO | 98/49659 A2 | 11/1998 |
| WO | 98/58693 A1 | 12/1998 |
| WO | 98/59487 A1 | 12/1998 |
| WO | 99/08183 A1 | 2/1999 |
| WO | 99/10801 A1 | 3/1999 |
| WO | 99/18532 A1 | 4/1999 |
| WO | 99/22236 A1 | 5/1999 |
| WO | 99/44655 A2 | 9/1999 |
| WO | 99/59663 A1 | 11/1999 |
| WO | 00/10628 A2 | 3/2000 |
| WO | 00/28217 A1 | 5/2000 |
| WO | 00/69493 A1 | 11/2000 |
| WO | 01/00261 A1 | 1/2001 |
| WO | 01/61616 A3 | 8/2001 |
| WO | 01/70304 A1 | 9/2001 |
| WO | 02/04047 A2 | 1/2002 |
| WO | 02/24257 A1 | 3/2002 |
| WO | 02/49509 A2 | 6/2002 |
| WO | 02/053220 A2 | 7/2002 |
| WO | 02/056945 A2 | 7/2002 |
| WO | 02/070049 A1 | 9/2002 |
| WO | 02/083209 A1 | 10/2002 |
| WO | 03/053498 A2 | 7/2003 |
| WO | 03/059422 A1 | 7/2003 |
| WO | 03/063932 A2 | 8/2003 |
| WO | 03/071930 A2 | 9/2003 |
| WO | 03/090838 A1 | 11/2003 |
| WO | 03/094075 A1 | 11/2003 |
| WO | 2004/007133 A1 | 1/2004 |
| WO | 2004/008956 A2 | 1/2004 |
| WO | 2004/009160 A1 | 1/2004 |
| WO | 2004006981 A2 | 1/2004 |
| WO | 2004-028596 A1 | 4/2004 |
| WO | 2004/058327 A2 | 7/2004 |

(56) References Cited

FOREIGN PATENT DOCUMENTS

| | | | |
|---|---|---|---|
| WO | 2004/069095 | A2 | 8/2004 |
| WO | 2004/070548 | A2 | 8/2004 |
| WO | 2004/070557 | A2 | 8/2004 |
| WO | 2004/070994 | A2 | 8/2004 |
| WO | 2004/070995 | A2 | 8/2004 |
| WO | 2004/098390 | A2 | 11/2004 |
| WO | 2005/000378 | A2 | 1/2005 |
| WO | 2005/010796 | A2 | 2/2005 |
| WO | 2005/016411 | A2 | 2/2005 |
| WO | 2005/019766 | A2 | 3/2005 |
| WO | 2005/019987 | A2 | 3/2005 |
| WO | 2005/039671 | A2 | 5/2005 |
| WO | 2005/094920 | A1 | 10/2005 |
| WO | 2005/101279 | A2 | 10/2005 |
| WO | 2005-102416 | A1 | 11/2005 |
| WO | 2005/112899 | A2 | 12/2005 |
| WO | 2005/121938 | A2 | 12/2005 |
| WO | 2006/001929 | A1 | 1/2006 |
| WO | 2006/023147 | A2 | 3/2006 |
| WO | 2006/032652 | A1 | 3/2006 |
| WO | 2006/081975 | A1 | 8/2006 |
| WO | 2006/083831 | A1 | 8/2006 |
| WO | 2006/097453 | A1 | 9/2006 |
| WO | 2006/108809 | A1 | 10/2006 |
| WO | 2007/016145 | A1 | 2/2007 |
| WO | 2007/094833 | A1 | 8/2007 |
| WO | 2009/083600 | A1 | 7/2009 |

OTHER PUBLICATIONS

International Search Report and Written Opinion From Corresponding International Application No. PCT/US2007/003490, dated Nov. 28, 2007 (20 pages).

International Search Report and Written Opinion From Corresponding International Application No. PCT/US2007/003567, dated Oct. 17, 2007 (18 pages).

International Search Report and Written Opinion From Corresponding International Application No. PCT/US2007/003587, Nov. 12, 2007 (18 pages).

International Search Report and Written Opinion From Corresponding International Application No. PCT/US2007/003634, Oct. 2, 2007 (18 pages).

International Search Report From Corresponding International Application No. PCT/US2009/060158, dated Mar. 23, 2010 (7 pages).

International Search Report and Written Opinion From Corresponding International Application No. PCT/US2009/093169, dated Mar. 31, 2010 (23 pages).

International Preliminary Report on Patentability From Corresponding International Application No. PCT/US2007/003567, dated Aug. 21, 2008 (11 pages).

Extended European Search Report From European Application No. 09075460.7, dated Mar. 5, 2010 (14 pages).

Office Action from Japanese Appln. No. 2002-591067 dated Jun. 10, 2008 (4 pages).

Non-final Office Action from corresponding U.S. Appl. No. 12/249,891, dated Nov. 18, 2009 (15 pages).

Conical fittings with a 6% (Luer) taper for syringes, needles and certain other medical equipment—Lock fittings, British Standard, BS EN 1707: 1997 (20 pages).

Conical fittings with a 6% (Luer) taper for syringes, needles and certain other medical equipment, Part 1. General requirements, British Standard, BS EN 20594-1 : 1994 ISO 594-1 : 1986 (17 pages).

Search Report from corresponding EP Appln. No. 10075446.4 dated Aug. 25, 2011 (10 pages).

Search Report from corresponding International Appln. No. PCT/US2011/030553 dated Dec. 23, 2011 (12 pages).

\* cited by examiner

MEDIUM CONNECTOR

TECHNICAL FIELD

This disclosure relates to medium connectors, and more particularly to medium connectors which may allow the engagement force between mating connectors to be regulated.

BACKGROUND OF THE DISCLOSURE

Medical device systems, such as medication delivery systems, frequently require various components to be fluidly connected to one another. For example, a syringe may be fluidly connected to an injection needle, an intravenous fluid supply bag may be fluidly connected to a catheter, etc. The fluid connections between the different components must be secure to prevent leakage as well as to prevent foreign substances, including air, from being introduced into the system. Additionally, it is often desirable to be able to quickly and easily make the desired connections without the user of tools One prevalent connection configuration in the medical device field is the Luer connection. Luer connections include cooperating male and female connector components having complimentary tapers. The taper geometry of Luer connectors are standardized as a continuous 6% taper. Connection between male and female Luer connectors may be made by pressing the male connector component into the female connector component. A friction fit is achieved between complimentary tapers of the connector components.

While Luer connectors provide reliable connection integrity and are relatively easy to use, no standardized tolerance is specified for the connector components. Slight deviations from an exact 6% taper may occur, e.g., as a result of manufacturing variation. Given that Luer connector components are often made of plastic materials, reliable connections are still achievable with connectors deviating slightly from the specified 6% taper, e.g., as a result of deformation of the plastic connector components and the relatively large contacting surface area. However, the depth of insertion of the connector components may vary as a result of any deviation from a 6% taper.

As such, when a defined insertion depth is required between the connector components, while a reliable connection may be achievable, the required insertion depth may not. The insertion depth of the connectors could be increased, e.g., by slightly deforming one or more of the connector components by pushing the connector components together more firmly. However, the constant taper of the connector components (resulting in an ever-increasing contact area), and the attendant engagement force, causes the insertion force to rapidly increase. It is possible that the engagement force may increase to a level that is greater than a force that is easily achievable by the user of the device, which may include elderly patients and/or patients having diminished physical capacity.

SUMMARY OF THE DISCLOSURE

According to a first implementation, a medium connector includes a passage configured to allow for the flow of medium, and a multi-portion engagement surface positioned about the passage. The multi-portion engagement surface includes a first surface portion, and a second surface portion. The first surface portion is configured to provide an interference fit with a corresponding sealing surface of a mating connector. The second surface portion is configured to provide a clearance fit with the corresponding sealing surface of the mating connector. The ratio of the first surface portion and the second surface portion is selected to regulate an engagement force between the medium connector and the mating connector.

One or more of the following features may be included. The mating connector may include a Luer taper connector. The multi-portion engagement surface may include a tapered surface, in which the first surface portion may have a first taper angle, and the second surface portion may have a second taper angle that is less than the first taper angle. Further, the second surface portion may be generally cylindrical. The multi-portion engagement surface may include a tapered surface, in which the first surface portion may have a first taper angle, and the second surface portion may have a second taper angle that is greater than the first taper angle. The second surface portion may include one or more recesses. The one or more recesses may include one or more radial slots. The one or more recesses may include one or more longitudinal slots.

The medium connector may include one or more retention features. The one or more retention features may include one or more snap-fit features.

According to another implementation, a medium connector includes a passage configured to allow for the flow of medium, and a tapered multi-portion engagement surface positioned about the passage. The multi-portion engagement surface includes a first surface portion, and a second surface portion. The first surface portion has a first taper angle configured to provide an interference fit with a corresponding sealing surface of a mating connector. The second surface portion has a second taper angle configured to provide a clearance fit with the corresponding sealing surface of the mating connector. The ratio of the first surface portion and the second surface portion is selected to regulate an engagement force between the medium connector and the mating connector.

One or more of the following features may be included. The mating connector may include a Luer taper connector. The second taper angle may be less that the first taper angle. The second surface portion may be generally cylindrical. The second taper angle may be greater than the first taper angle. The medium connector may include one or more retention features. The one or more retention features may include a snap fit feature.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF PREFERRED EMBODIMENT

Figure 1A:
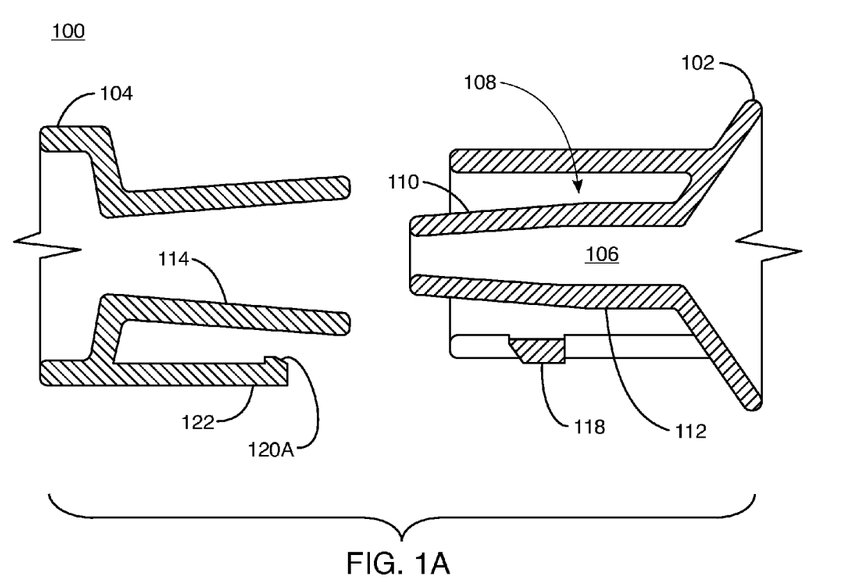
FIG. 1A diagrammatically depicts a first embodiment of a medium connector assembly, including a medium connector and a mating connector in a dis-engaged configuration.

Referring to FIG. 1A, there is shown a medium connector assembly 100 for connecting medium carrying components (not shown) and allowing the flow of medium therebetween. Examples of medium carrying components may include, but are not limited to, a delivery catheter and an insulin delivery pump, a fluid supply (such as an intravenous fluid supply bag, a dialysate supply, etc.) and a pump supply catheter, or the like. Connector assembly 100 may include medium connector 102 associated with a first medium carrying component (not shown) and mating connector 104 associated with a second medium carrying component.

Medium connector 102 may include passage 106 to allow for the flow of medium. The medium flowing between the medium carrying components, e.g., via passage 106, may include liquids (e.g., insulin, dialysate, saline solution, or the like), gases (e.g., air, oxygen, nitrogen, or the like), suspensions, or the like. Further, medium connector 102 may include multi-portion engagement surface 108, generally, positioned about passage 106. Multi-portion engagement surface 108 may include first surface portion 110, and second surface portion 112.

As will be discussed in greater detail below, first surface portion 110 of multi-portion engagement surface 108 may be configured to provide an interference fit with corresponding sealing surface 114 of mating connector 104. Further, second surface portion 112 of multi-portion engagement surface 108 may be configured to provide a clearance fit with corresponding sealing surface 114 of mating connector 104. The ratio of first surface portion 110 and second surface portion 112 may be selected to regulate an engagement between medium connector 102 and mating connector 104.

For example, corresponding sealing surface 114 of mating connector 104 may include a tapered surface, e.g., which may include a 6% taper (e.g., approximately 3.4 degree included taper) of a standard Luer taper connector (e.g., as defined by the ISO 594 standard). Of course, corresponding sealing surface 114 may include tapers other than a 6% Luer taper. Multi-portion engagement surface 108 may similarly include a tapered surface, in which first surface portion 110 may have a first taper angle, and second surface portion 112 may have a second taper angle that is less than the first taper angle. In one particular embodiment, the second taper angle may approach zero, such that second surface portion 112 may be generally cylindrical (e.g., may include a slight taper, such as a draft angle to facilitate manufacture). Of course, second surface portion 112 may include other, non-cylindrical, taper angles.

Figure 1B:
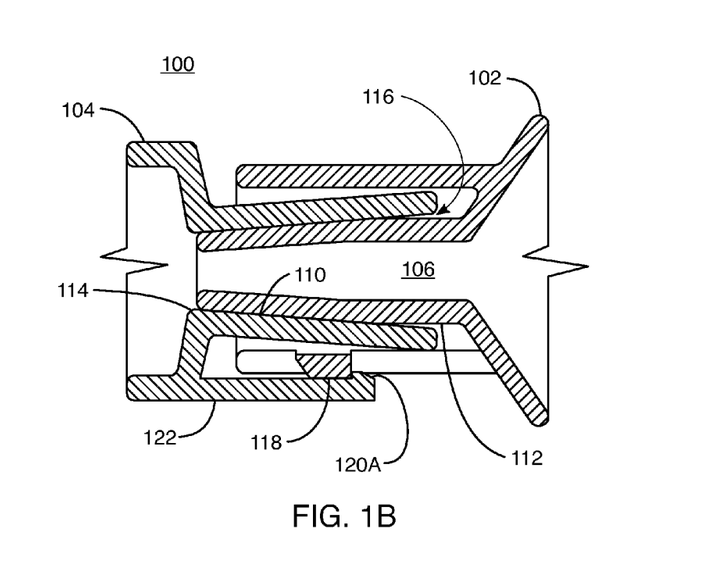
FIG. 1B diagrammatically depicts the first embodiment of the medium connector assembly of FIG. 1A in an engaged configuration.

Continuing with the above-stated example, first surface portion 110 of multi-portion engagement surface 108 may include a first taper angle corresponding to the angle of corresponding sealing surface 114 of mating connector 104 (e.g., a 6% taper). As shown in FIG. 1B, the corresponding taper of first surface portion 110 may provide an interference fit with corresponding sealing surface 114 of mating connector 104. As also shown, the second taper angle of second surface portion 112 may provide a clearance fit with corresponding sealing surface 114 of mating connector 104, e.g., which may result in at least partial clearance 116 between second surface portion 112 and corresponding sealing surface 114.

The contact surface area of medium connector 102 and mating connector 104 may remain generally constant once first surface portion 110 has engaged corresponding sealing surface 114. For example, as first surface portion 110 may be configured to provide an interference fit with corresponding sealing surface 114, while second surface portion 112 of multi-portion engagement surface 108 may be configured to provide a clearance fit with corresponding sealing surface 114, only first surface portion 110 may engage corresponding sealing surface 114.

Once first surface portion 110 engages corresponding sealing surface 114, further insertion of medium connector 102 relative to mating connector 104 may be attributable to the elastic and/or plastic deformation force of medium connector 102 in the region of first surface portion 110 and/or of mating connector 104 in the region of contact between corresponding sealing surface 114 and first surface portion 110 (e.g., as first surface portion 110 is forced into the progressively smaller opening provided by corresponding sealing surface 114), and the frictional interaction between first surface portion 110 and corresponding sealing surface 114 of mating connector 104.

As such, the ratio of first surface portion 110 and second surface portion 112 may be selected to regulate an engagement force between medium connector 102 and mating connector 104. As discussed above, second surface portion 112 may be configured to provide a clearance fit with corresponding sealing surface 114, and as such may not contribute to the engagement force (e.g., the insertion force per increment of axial insertion) between medium connector 102 and mating connector 104. Therefore, the ratio of first surface portion 110 to second surface portion 112 may be increased to increase the engagement force between medium connector 102 and mating connector 104. Conversely, the ratio of first surface portion 110 to second surface portion 112 may be decreased to decrease the engagement force between medium connector 102 and mating connector 104.

The ability to regulate the engagement force between medium connector 102 and mating connector 104 (e.g., based upon the ratio of first surface portion 110 and second surface portion 112) may allow the use of features associated with medium connector 102 (and/or the first associated medium carrying component) and/or mating connector 104 (and/or the second associated medium carrying component) which may require a minimum insertion depth to be achieved within a selected range of insertion forces. For example, medium connector 102 may include one or more retention features, e.g., which may facilitate a positive engagement and/or relative position between medium connector 102 and mating connector 104. As shown in FIGS. 1A and 1B, the one or more retention features may include one or more snap-fit features (e.g., cooperating snap-fit features 118, 120A, respectively associated with medium connector 102 and mating connector 104). As shown, one or more of cooperating snap-fit features 118, 120A may be disposed on a cantilever feature (e.g., cantilever arm 122), e.g., which may facilitate engagement/dis-engagement of cooperating snap fit features 118, 120A. Snap-fit features 118, 120A may require a minimum insertion depth to provide engagement therebetween. As described above, the ratio of first surface portion 110 and second surface portion 112 may be selected to regulate the engagement force between medium connector 102 and mating connector 104 associated with the insertion depth necessary to provide engagement between snap-fit features 118, 120A. While regulating the engagement force between the medium connector and the mating connector has been described in connection with the use of retention features, this is not intended as a limitation of the present disclosure, as the ability to regulate the engagement force between the medium connector and the mating connector may equally be used for other purposes.

Figure 2A:
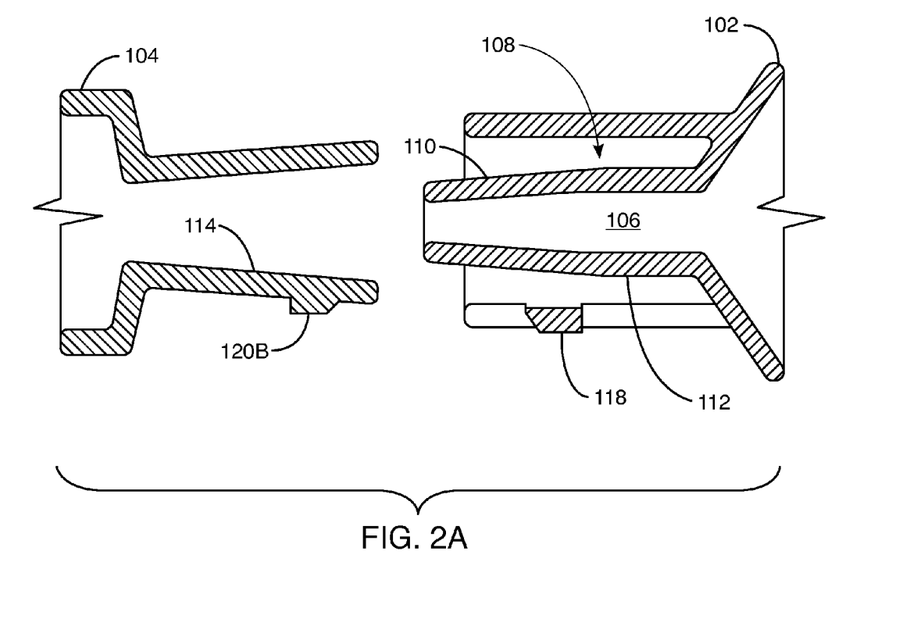
FIG. 2A diagrammatically depicts another embodiment of a medium connector assembly, including a medium connector and a mating connector in a dis-engaged configuration.
Figure 2B:
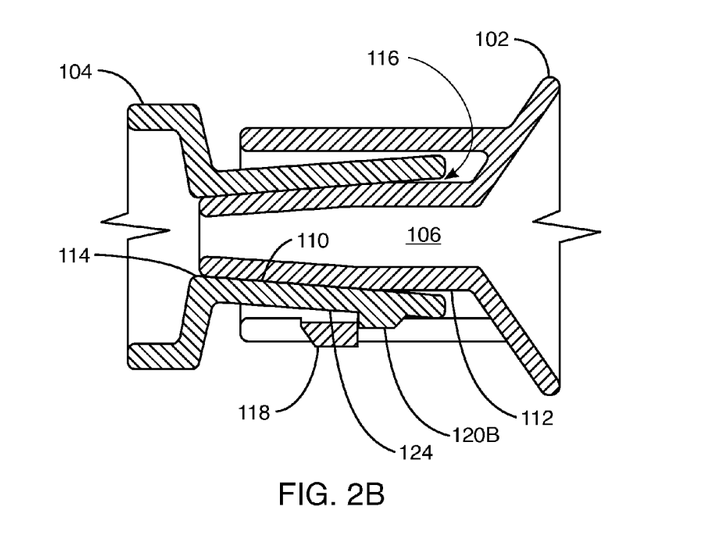
FIG. 2B diagrammatically depicts the medium connector assembly of FIG. 2A in an engaged configuration.

Referring also to FIGS. 2A and 2B, in a related embodiment, the medium connector assembly may include medium connector 102 associated with a first medium carrying component (not shown) and mating connector 104 associated with a second medium carrying component. As shown, one or more of the cooperating snap-fit features (e.g., cooperating snap-fit features 118, 120B) may be provided as a feature associated with one of the mating surfaces of the medium connector assembly (e.g., snap-fit feature 120b may be formed on member 124 defining corresponding sealing surface 114). Based upon, at least in part, the illustrated exemplary embodiments of FIGS. 1A-1B and 2A-2B, various additional/alternative arrangements may be readily understood, and are contemplated by the present disclosure.

Figure 3:
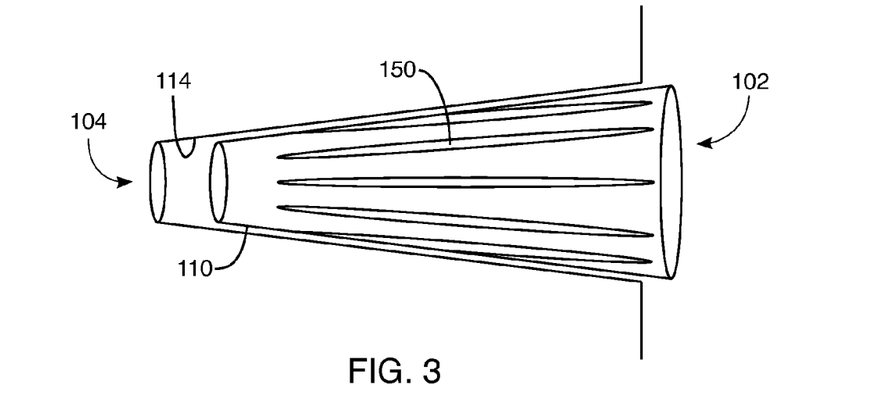
FIG. 3 diagrammatically depicts another embodiment of a medium connector assembly.

In addition/as an alternative to the second surface portion including a second taper angle, the second surface portion may include one or more recesses. For example, and referring also to FIG. 3, the second surface portion may include one or more recesses including one or more longitudinal slots (e.g., longitudinal slot 150), e.g., which may be formed in first surface portion 110. Longitudinal slot 150 may be configured to provide a clearance fit with cooperating sealing surface 114 of mating connector 104. For example, longitudinal slot 150 may provide a second surface portion which may not engage cooperating sealing surface 114 when first surface portion 110 is fully engaged with cooperating sealing surface 114 of mating connector 104. The ratio of first surface portion 110 and the radial slots (e.g., longitudinal slot 150) may be selected to regulate the engagement force between medium connector 102 and mating connector 104, e.g., in as much as longitudinal slot 150 may not provide a frictional engagement force with cooperating sealing surface 114 of mating connector 104.

Figure 4:
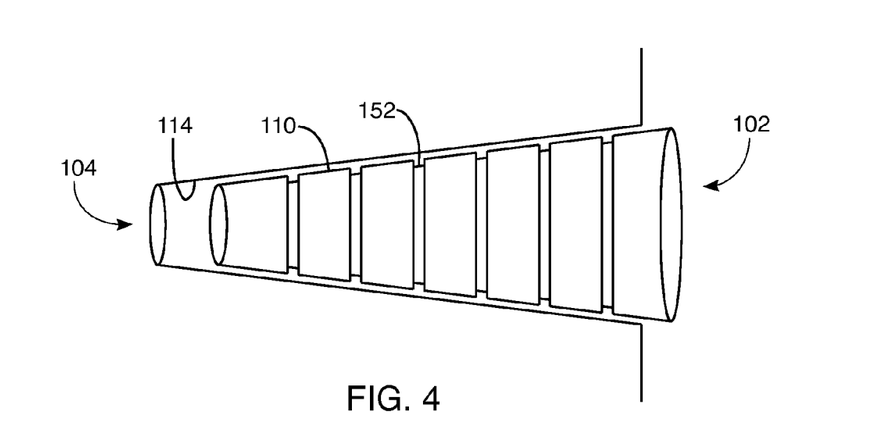
FIG. 4 diagrammatically depicts another embodiment of a medium connector assembly.

Referring also to FIG. 4, additionally/alternatively the second surface portion may include one or more recesses that may include one or more radial slots (e.g., radial slot 152). Similar to the above-described longitudinal slots (e.g., longitudinal slot 150), radial slot 152 may be configured to provide a clearance fit with corresponding sealing surface 114 of mating connector 104. As such, the ratio of first surface portion 110 and the radial slots (e.g., radial slot 152) may be selected to regulate the engagement force between medium connector 102 and mating connector 104. For example, radial slot 152 may not provide a frictional engagement force with cooperating sealing surface 114 of mating connector 104.

In addition to the specifically described and depicted recesses in the form of longitudinal slots and radial slots, the one or more recesses may include various additional and/or alternative configurations (e.g., dimples, etc.), which may be configured to provide a clearance fit with the cooperating sealing surface of the mating connector. As such, the ratio of the first surface portion and the second surface portion (including one or more recesses) may be selected to regulate an engagement force between the medium connector and the mating connector. Further, it will be appreciated that the number, arrangement, and character of the one or more recesses may vary according to design criteria and preference.

Figure 5:
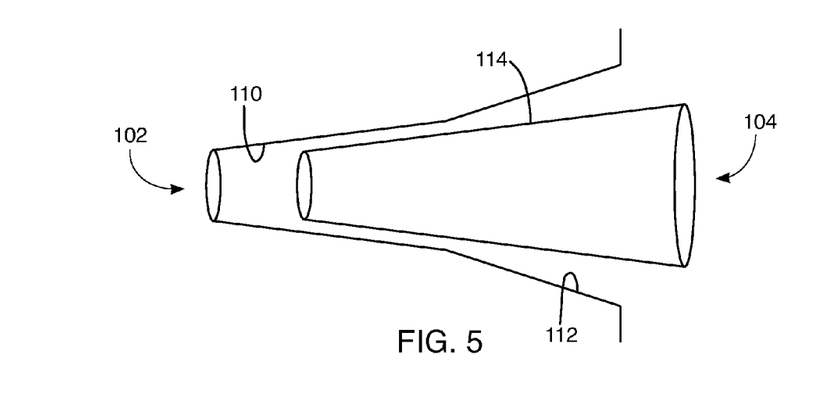
FIG. 5 diagrammatically depicts another embodiment of a medium connector assembly.
Figure 6A:
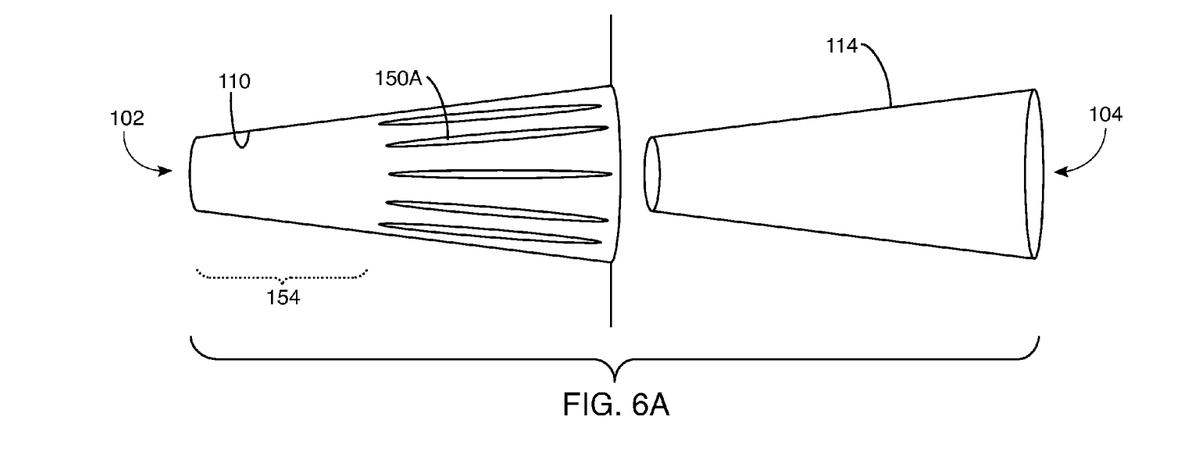
FIGS. 6A and 6B diagrammatically depict another embodiment of a medium connector assembly.
Figure 6B:
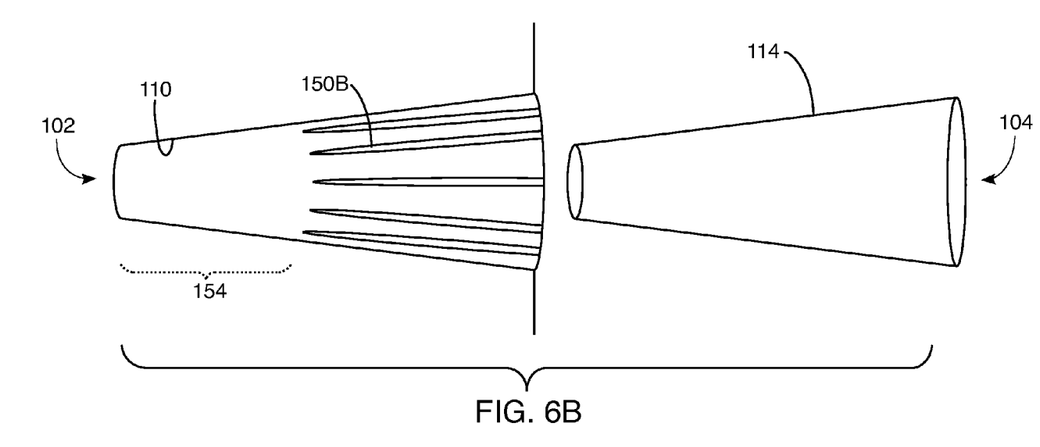
Figure 7:
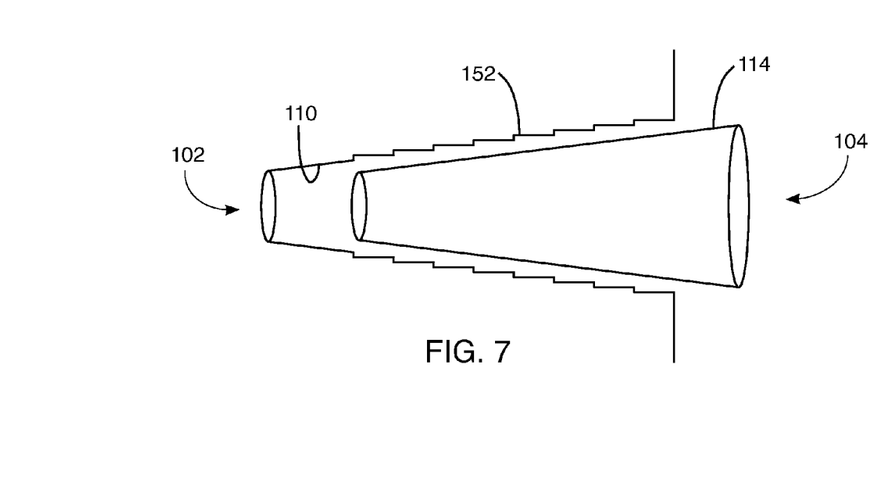
FIG. 7 diagrammatically depicts another embodiment of a medium connector.

While the above-described embodiments have been depicted having a multi-portion engagement surface configured as a male medium connector portion, referring also to FIGS. 5 through 7, medium connector 102 may additionally/alternatively be configured as a female connector portion. For example, medium connector 102 may include a female connector portion having a multi-portion engagement surface including first surface portion 110 and second surface portion 112. As shown in FIG. 5, the multi-portion engagement surface may include a tapered surface, in which first surface portion 110 may have a first taper angle configured to provide an interference fit with cooperating sealing surface 114 of male mating connector 104. Further, second surface portion 112 may have a second taper angle that is greater than the first taper angle. As such, second surface portion 112 may be configured to provide a clearance fit with cooperating sealing surface 114 of male mating connector 104.

Further, the second surface portion may include one or more recesses. For example, and referring also to FIGS. 6A and 6B, the one or more recesses may include one or more longitudinal slots (e.g., longitudinal slot 150A, 150B). Similar to previously described embodiments, first surface portion 110 may be configured to provide an interference fit with cooperating sealing surface 114 of male mating connector 104. Further, the second surface portion, including longitudinal slot 150A, 150B, may be configured to provide a clearance fit with cooperating sealing surface 114 of male mating connector 104. Medium connector 102 may include sealing region 154, which may not include longitudinal slots, e.g., to thereby facilitate achieving a seal between first surface portion 110 and cooperating sealing surface 114 of mating connector 104.

Referring also to FIG. 7, the second surface portion may include one or more recesses, in which the one or more recesses may include one or more radial slots (e.g., radial slot 152). Radial slot 152 may be configured to provide a clearance fit with cooperating sealing surface 114 of male mating connector 104.

In addition to the specifically described and depicted recesses in the form of longitudinal slots and radial slots, the one or more recesses may include various additional and/or alternative configurations (e.g., dimples, etc.), which may be configured to provide a clearance fit with the cooperating sealing surface of the mating connector. As such, the ratio of the first surface portion and the second surface portion (including one or more recesses) may be selected to regulate an engagement force between the medium connector and the mating connector. Further, it will be appreciated that the number, arrangement, and character of the one or more recesses may vary according to design criteria and preference.

A number of implementations have been described. Nevertheless, it will be understood that various modifications may be made. Accordingly, other implementations are within the scope of the following claims.

What is claimed is:
1. A combination comprising:
 a medium connector comprising:
  a passage allowing the flow of medium therethrough;
  a multi-portion engagement surface positioned about the passage, the multi-portion engagement surface including:
   a first surface extending along a first portion of the length of the passage, and
   a second surface extending along a second portion of the length of the passage;
   wherein the first surface is arranged at a first taper angle relative to a centerline of the passage and the second surface is arranged at a second taper angle relative to the centerline of the passage, wherein the first taper angle and the second taper angle are different; and a cantilever feature disposed about the multi-portion engagement surface, the cantilever feature including a first retention feature formed on an outer surface thereof; and a mating connector comprising:

a sealing surface configured to engage the medium connector; and a cantilever arm extending adjacent to the sealing surface, the cantilever arm having a second retention feature formed at a distal end thereof;

wherein the first surface of the medium connector provides an interference fit with the sealing surface of the mating connector and the second surface of the medium connector provides a clearance fit with the sealing surface of the mating connector;

wherein the ratio of the first surface and the second surface is selected to regulate an engagement force between the medium connector and the mating connector;

wherein the passage of the medium connector is adapted to be fluidly coupled to the mating connector to allow the medium to flow through the passage of the medium connector and to exit the passage into the mating connector when the medium connector is engaged with the mating connector;

wherein the interference fit between the sealing surface of the mating connector and the first surface of the medium connector prevents leakage of the medium flowing through the passage of the medium connector and into the mating connector as the medium passes from the medium connector to the mating connector through the passage; and wherein the cantilever feature of the medium connector is adapted to be disposed between the sealing surface and the cantilever arm of the mating connector with the second retention feature on the cantilever arm engaging the first retention feature on the outer surface of the cantilever feature.

2. The combination according to claim 1, wherein the mating connector includes a Luer taper connector.

3. The combination according to claim 1, wherein the second taper angle is less than the first taper angle.

4. The combination according to claim 3, wherein the second surface is generally cylindrical.

5. The medium connector of claim 1, wherein the multi-portion engagement surface includes a tapered surface, the first surface portion having a first taper angle, and the second surface portion having a second taper angle that is greater than the first taper angle.

6. The combination according to claim 1, wherein the first and second retention features include snap-fit features.

7. A combination comprising:
a medium connector comprising:
a passage allowing the flow of medium therethrough;
a tapered multi-portion engagement surface positioned about the passage, the tapered multi-portion engagement surface including:
a first surface extending along a first portion of the length of the passage, and a second surface extending along a second portion of the length of the passage;

wherein the first surface is arranged at a first taper angle relative to a centerline of the passage and the second surface is arranged at a second taper angle relative to the centerline of the passage, wherein the first taper angle and the second taper angle are different; and a cantilever feature disposed about the tapered multi-portion engagement surface, the cantilever feature including a first retention feature formed on an outer surface thereof; and a mating connector comprising:

a sealing surface configured to engage the medium connector; and a cantilever arm extending adjacent to the sealing surface, the cantilever arm having a second retention feature formed at a distal end thereof;

wherein the first taper angle of the first surface provides an interference fit with the sealing surface of the mating connector and the second taper angle of the second surface provides a clearance fit with the sealing surface of the mating connector;

wherein the ratio of the first surface and the second surface is selected to regulate an engagement force between the medium connector and the mating connector;

wherein the passage of the medium connector is adapted to be fluidly coupled to the mating connector to allow the medium to flow through the passage of the medium connector and to exit the passage into the mating connector when the medium connector is engaged with the mating connector;

wherein the interference fit between the sealing surface of the mating connector and the first surface of the medium connector prevents leakage of the medium flowing through the passage of the medium connector and into the mating connector as the medium passes from the medium connector to the mating connector through the passage; and wherein the cantilever feature of the medium connector is adapted to be disposed between the sealing surface and the cantilever arm of the mating connector with the second retention feature on the cantilever arm engaging the first retention feature on the outer surface of the cantilever feature.

8. The combination according to claim 7, wherein the mating connector includes a Luer taper connector.

9. The combination according to claim 7, wherein the second taper angle is less than the first taper angle.

10. The combination according to claim 9, wherein the second surface is generally cylindrical.

11. The medium connector of claim 7, wherein the second taper angle is greater than the first taper angle.

12. The combination according to claim 7, wherein the first and second retention features include snap fit features.

* * * * *

UNITED STATES PATENT AND TRADEMARK OFFICE
CERTIFICATE OF CORRECTION

| | | Page 1 of 1 |
|---|---|---|
| PATENT NO. | : 8,708,376 B2 | |
| APPLICATION NO. | : 12/249340 | |
| DATED | : April 29, 2014 | |
| INVENTOR(S) | : Tracey | |

It is certified that error appears in the above-identified patent and that said Letters Patent is hereby corrected as shown below:

On the title page item [56] should read:

--4,561,856--
--4,714,463--
--5,405,614--
--2009/0124994--

Signed and Sealed this
Fourteenth Day of October, 2014

Michelle K. Lee
*Deputy Director of the United States Patent and Trademark Office*